(12) United States Patent
Li

(10) Patent No.: US 11,877,718 B2
(45) Date of Patent: Jan. 23, 2024

(54) THROMBUS REMOVAL DEVICE

(71) Applicant: Lifetech Scientific (Shenzhen) Co., Ltd., Shenzhen (CN)

(72) Inventor: Siyi Li, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 47 days.

(21) Appl. No.: 17/299,454

(22) PCT Filed: Jul. 10, 2019

(86) PCT No.: PCT/CN2019/095335
§ 371 (c)(1),
(2) Date: Jun. 3, 2021

(87) PCT Pub. No.: WO2020/113957
PCT Pub. Date: Jun. 11, 2020

(65) Prior Publication Data
US 2022/0022897 A1 Jan. 27, 2022

(30) Foreign Application Priority Data
Dec. 5, 2018 (CN) .......................... 201811482200.X

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00477* (2013.01); *A61B 2017/2215* (2013.01); *A61B 2017/22038* (2013.01)

(58) Field of Classification Search
CPC ............ A61B 17/22031; A61B 17/221; A61B 17/320725; A61B 2017/00477;
(Continued)

(56) References Cited

U.S. PATENT DOCUMENTS 10,383,644 B2 8/2019 Moleai et al.
10,390,850 B2 8/2019 Vale et al.
(Continued)

FOREIGN PATENT DOCUMENTS

DE 2933266 A1 5/1981

OTHER PUBLICATIONS

Office Action dated Nov. 18, 2020 for corresponding China Application No. 201811482200.X.
(Continued)

*Primary Examiner* — Kankindi Rwego
(74) *Attorney, Agent, or Firm* — Raymond Sun

(57) ABSTRACT

The invention belongs to the field of interventional medical instruments, and relates in particular to a thrombus removal device used for removing a thrombus in a blood vessel. The thrombus removal device includes an elongated delivery member and a plurality of thrombus removal members disposed on the elongated delivery member; the thrombus removal member has a compressed configuration and an expanded configuration formed from the compressed configuration by means of self-expansion; and at least one thrombus removal member among the plurality of thrombus removal members is rotatably connected to the elongated delivery member. By means of causing the thrombus removal member to have rotational degrees of freedom, the thrombus removal device provided by the present invention enables a thrombus to enter the thrombus removal member more easily by means of a thrombus entrance so that the thrombus removal member may fully contact the thrombus, thereby achieving effective capture of the thrombus.

18 Claims, 13 Drawing Sheets

(58) Field of Classification Search
CPC .. A61B 2017/22038; A61B 2017/2212; A61B 2017/2215; A61B 2017/2217; A61B 2017/22034; A61B 2017/22035; A61B 2017/22039; A61F 2/011; A61F 2/012; A61F 2/013; A61F 2002/015; A61F 2002/016; A61F 2002/018
USPC ........................................................ 606/127
See application file for complete search history.

(56) References Cited

U.S. PATENT DOCUMENTS

| | | | |
|---|---|---|---|
| 10,537,344 B2 | 1/2020 | Davidson et al. | |
| 2002/0138094 A1* | 9/2002 | Borillo .................... | A61F 2/013 606/200 |
| 2004/0138692 A1 | 7/2004 | Phung | |
| 2005/0209631 A1* | 9/2005 | Galdonik ........ | A61M 25/09025 606/108 |
| 2007/0239201 A1 | 10/2007 | Phung et al. | |
| 2012/0016407 A1 | 1/2012 | Sakai | |
| 2013/0345739 A1* | 12/2013 | Brady ............ | A61B 17/320725 606/200 |
| 2015/0250497 A1* | 9/2015 | Marks .................. | A61B 17/221 606/159 |
| 2016/0058459 A1 | 3/2016 | Bowman | |
| 2016/0120558 A1 | 5/2016 | Brady et al. | |
| 2017/0150979 A1 | 6/2017 | Ulm, III | |
| 2017/0265876 A1 | 9/2017 | Ventures | |
| 2017/0265983 A1 | 9/2017 | Lam et al. | |
| 2018/0256179 A1 | 9/2018 | Hayakawa | |
| 2019/0380723 A1* | 12/2019 | Grandfield ........... | A61B 17/221 |

OTHER PUBLICATIONS

Translation for Office Action dated Nov. 18, 2020 for corresponding China Application No. 201811482200.X.
Response to Office Action dated Nov. 18, 2020 for corresponding China Application No. 201811482200.X.
Translation of Response to Office Action dated Nov. 18, 2020 for corresponding China Application No. 201811482200.X.
Notification of Grant dated May 18, 2021 for corresponding China Application No. 201811482200.X.
Translation of Notification of Grant dated May 18, 2021 for corresponding China Application No. 201811482200.X.
Office Action dated Oct. 31, 2017 for corresponding China Application No. 201811482200.X.
International Search Report dated Sep. 27, 2019 for corresponding PCT Application No. PCT/CN2019/095335.
Office Action dated Apr. 7, 2022 for corresponding European Application No. EP 19 89 3292.
Office Action dated Dec. 19, 2022 for corresponding Infda Application No. 202117025774.

* cited by examiner

THROMBUS REMOVAL DEVICE

TECHNICAL FIELD

The invention belongs to the field of interventional medical instruments, and relates in particular to a thrombus removal device used for removing a thrombus in a blood vessel.

BACKGROUND ART

Cerebral stroke is a common disease in medicine. China is a major country suffering from cerebral stroke in the world; and cerebral stroke has become the leading cause of death in China. Based on the related epidemiological studies, 3 out of 4 cerebral stroke patients suffer different degrees of disability. Acute ischemic stroke (AIS), commonly known as cerebral infarction, is a kind of neural tissue injury caused by regional cerebral ischemia and necrosis due to sudden occlusion of cerebral blood flow. AIS is the most common type of stroke, which is the leading cause of death and disability in the middle-aged and aged people. Revascularization is the key to the treatment of acute ischemic stroke. Currently, there are two major categories of conventional methods in the treatment of acute ischemic stroke: interventional thrombolysis and mechanical thrombus removal. Mechanical thrombus removal can quickly revascularize the occluded blood vessel to improve the revascularization rate, reduce the dosage of a thrombolytic drug, decrease the incidence of symptomatic cerebral hemorrhage, and prolong the therapeutic time window, thereby fighting for more time for reversible ischemic brain tissues and obviously improving the prognosis of patients.

At present, most of the thrombus removal devices sold in the market are integrated self-expandable thrombus removal stents, and the use procedure of these thrombus removal stents is described in FIGS. 1-3: a thrombus removal stent 101 is compressed into a microcatheter 102, a developing mark 103 is arranged on a distal end of the microcatheter 102; the developing mark 103 can show the position where the microcatheter 102 arrives under CT angiography (CTA), magnetic resonance angiography (MRA) and other equipment; and the proximal end of the thrombus removal stent 101 is connected to the push-pull wire 104. The microcatheter 102 passes through the blood vessel 201 from the proximal end to where the thrombus 202 is located, and passes through the thrombus 202 under the guidance of the guide wire 105 through the minimally invasive surgery. The push-pull wire 104 fixed and the microcatheter 102 is withdrawn, so that the thrombus removal stent 101 is pushed out of the microcatheter 102 and expanded; and the push-pull wire 104 is fixed for about five minutes so that the thrombus removal stent 101 fully expands; and a grid bar of the thrombus removal stent 101 permeates into the thrombus 202 and fully contacts the thrombus 202 by the self-expansion radial force of the thrombus removal stent 101. Afterwards, the push-pull wire 104 is withdrawn, and through the pulling of the push-pull wire 104, the thrombus removal stent 101 drives the thrombus 202 to move towards the operator until the thrombus removal stent 101 and the captured thrombus 202 are together dragged into a retrieval catheter 106 (a developing mark 107 may be disposed at a distal end of the retrieval catheter 106); and the retrieval catheter 106, and the thrombus removal stent 101, push-pull wire 104 and the thrombus 202 in the retrieval catheter 106 are proximally withdrawn out of the body of a patient.

During the procedure described above, the above integrated self-expandable thrombus removal stent can extrude the thrombus by virtue of the radial force itself, so that the thrombus can enter the interior of the stent through the grid of the stent to achieve the capture of the thrombus. However, there are the following problems in the existing integrated thrombus removal stent:

First, grids of the thrombus removal stent are the channels for the thrombus to enter the interior stent, so the size of the grids determines the capture effect of the thrombus removal stent. Generally, an integrated thrombus removal stent has the largest grid size in a full expansion state, while the thrombus removal stent is always in a compressed state in a blood vessel, which means that the grids of the thrombus removal stent are not in an optimal size, especially when used in capturing leukocyte-enriched pale/hard thrombus (the thrombus is rich in fibers and has strong viscoelasticity; studies have shown that the force required to compress the leukocyte-enriched pale/hard thrombus pale/hard thrombus is 9 mN/mm2). However, the radial force of the self-expandable stent is not sufficient to allow the grid bar of the stent to penetrate into the pale thrombus; and the grid size of the thrombus removal stent cannot allow the pale thrombus to enter the thrombus removal stent from the grids.

Second, local deformation of the thrombus removal stent will cause the deformation of the grids associated with the deformed portion. Consequently, the thrombus removal stent decreases in its overall diameter when it passes through sections of bent blood vessels during the withdrawal process, so that the thrombus removal stent may be separated from the blood vessel, and the thrombus may fall off from the stent.

SUMMARY OF THE INVENTION

In view of the above problems, an objective of the present disclosure is to provide a thrombus removal device capable of effectively capturing various kinds of thrombi; and the objective is achieved by the following technical solutions:

The present disclosure provides a thrombus removal device, including an elongated delivery member and a plurality of thrombus removal members disposed on the elongated delivery member; where the thrombus removal member has a compressed configuration and an expanded configuration formed from the compressed configuration by means of self-expansion; and at least one thrombus removal member among the plurality of thrombus removal members is rotatably connected to the elongated delivery member.

The disclosure has the following advantages:

By means of causing the thrombus removal member to have rotational degrees of freedom, the thrombus removal device provided by the present disclosure enables a thrombus to enter the thrombus removal member more easily by means of a thrombus entrance so that the thrombus removal member may fully expand and fully contact the thrombus, thereby achieving more effective capture of the thrombus.

BRIEF DESCRIPTION OF THE DRAWINGS

The drawings are only for the purpose of showing the preferred embodiments and are not for limiting the present disclosure. Moreover, in the entire drawings, same reference numerals denote the same parts. In the drawings.

DETAILED DESCRIPTION OF THE INVENTION

Figure 1:
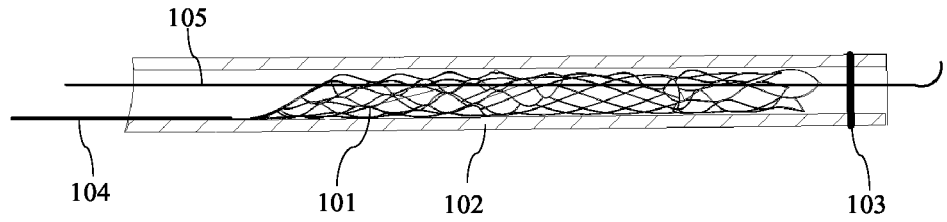
FIG. 1 is a schematic diagram showing an integrated self-expandable thrombus removal stent in the prior art compressed into a microcatheter.
Figure 2:
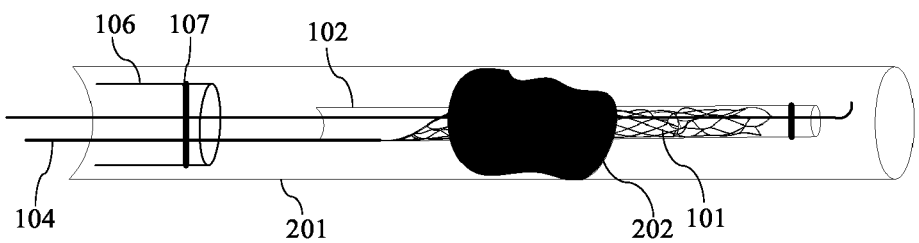
FIG. 2 is a schematic diagram showing that the thrombus removal stent and microcatheter as shown in FIG. 1 is passed through a thrombus.
Figure 3:
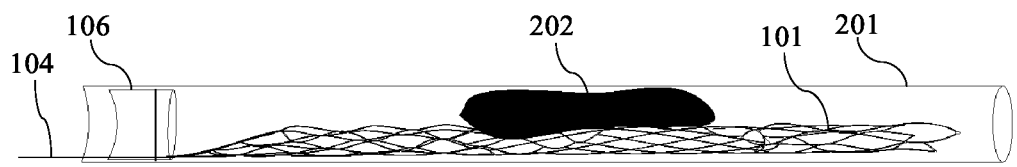
FIG. 3 is a schematic diagram showing the thrombus removal stent gradually penetrating into the thrombus after the microcatheter as shown in FIG. 2 is withdrawn.
Figure 4:
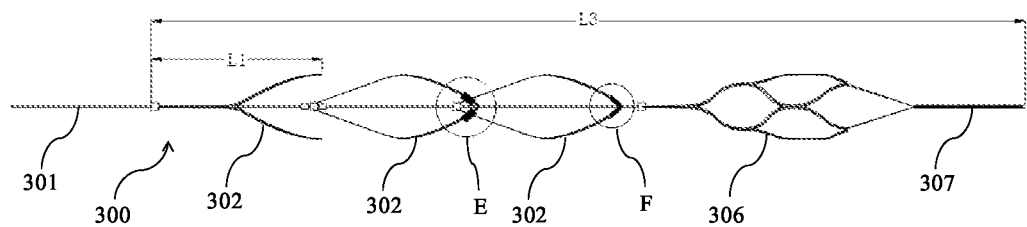
FIG. 4 is a schematic diagram showing a structure of the thrombus removal device in Example 1.
Figure 5:
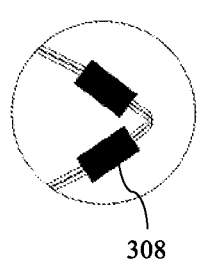
FIG. 5 is a schematic diagram showing an enlarged portion E in FIG. 4.
Figure 6:
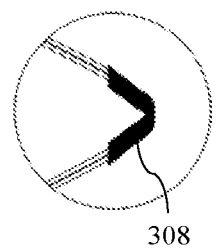
FIG. 6 is a schematic diagram showing an enlarged portion F in FIG. 4.
Figure 7:
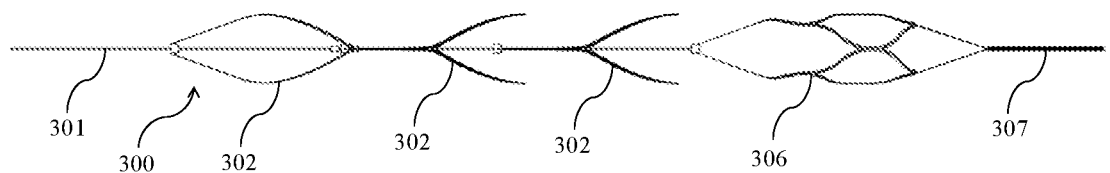
FIG. 7 is a top schematic view of FIG. 4.
Figure 8:
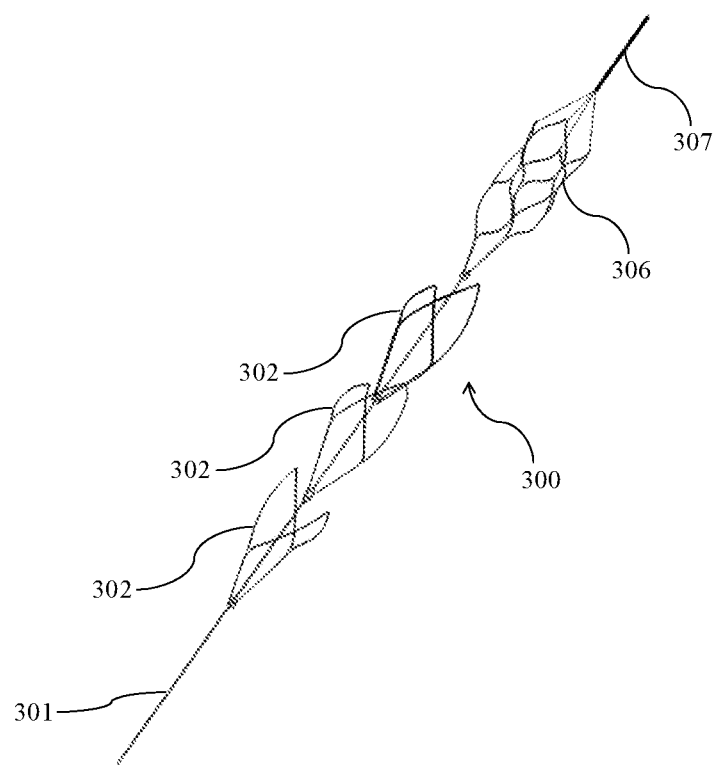
FIG. 8 is a 3D schematic diagram of the thrombus removal device in Example 1.
Figure 9:
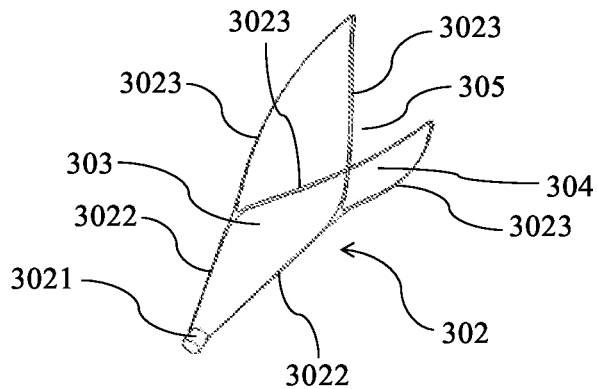
FIG. 9 is a 3D schematic diagram of the thrombus removal member in Example 1.
Figure 10:
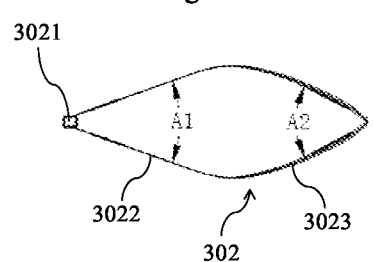
FIG. 10 is a schematic front view of the thrombus removal member as shown in FIG. 9.
Figure 11:
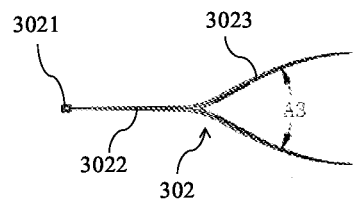
FIG. 11 is a top schematic diagram of FIG. 10.
Figure 12:
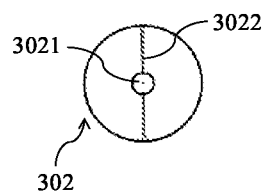
FIG. 12 is a side schematic diagram of FIG. 10.
Figure 13A:
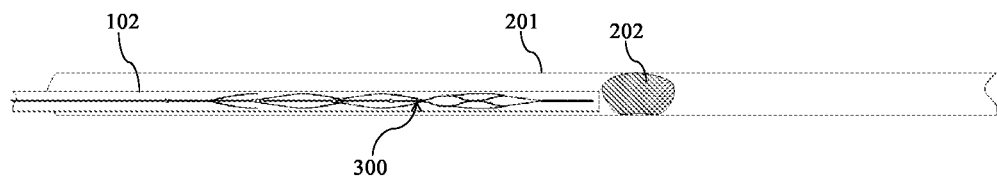
FIG. 13 is a schematic diagram showing the thrombus removal operation by using the thrombus removal device in Example 1, where FIG. (a) shows that a microcatheter containing a thrombus removal device is delivered to the location of the thrombus in a blood vessel; FIG. (b) shows that the microcatheter passes through the thrombus and is positioned into a more distal location in the blood vessel; FIG. (c) shows that the thrombus removal device gradually expands after being released; FIG. (d) shows that an elongated delivery member is pushed/pulled to make the thrombus removal member rotate under the acting force of the thrombus and blood vessel; and FIG. (e) shows that the thrombus removal member expands fully and the thrombus enters a grid frame by means of a thrombus entrance.
Figure 13B:
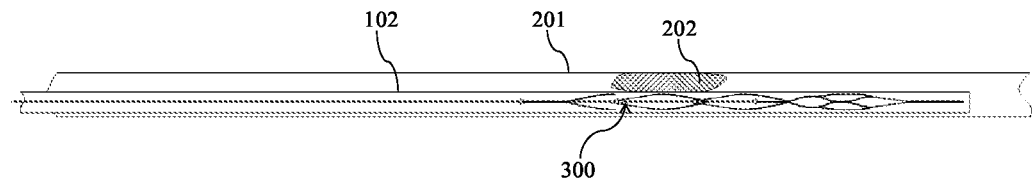
Figure 13C:
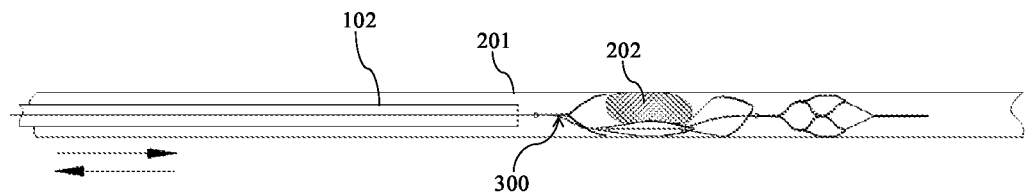
Figure 13D:
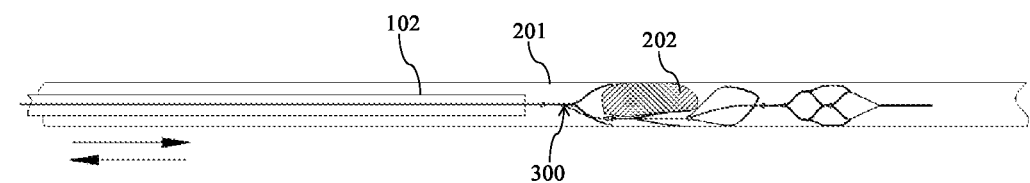
Figure 13E:
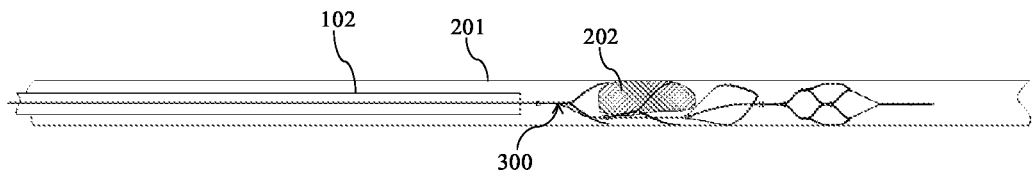

The exemplary embodiments of the present disclosure will be explained in detail with reference to the accompanying drawings. Even although exemplary embodiments of the present disclosure are shown in the drawings, it should be understood that the present disclosure may be embodied in various forms but should not be limited to the embodiments set forth herein. Rather, these embodiments are provided so that present disclosure will be understood more thoroughly; and the scope of the present disclosure will be fully conveyed to those skilled in the art.

It should be understood that the terms used herein are only for the purpose of describing particular exemplary embodiments and are not intended to limit the present disclosure. The singular forms "a/an", and "one" and "the", as used herein, are intended to denote including the plural forms as well, unless otherwise specified in the context explicitly. The terms "comprising", "including", "containing", and "having" are inclusive and thus specify the presence of the features, steps, operations, elements, and/or components stated therein, but it is not exclusive of the presence or addition of one or more other features, steps, operations, elements, components, and/or combinations thereof. The steps, processes, and operations described herein are not to be construed as necessarily requiring them to be executed in the particular order described or specified herein, unless the order of execution is explicitly indicated. It should also be understood that additional or alternative steps may be used.

A plurality of elements, components, regions, layers and/or sections may be described by using the terms first, second, third, and the like, but shall be not limited by these terms. These terms may be used merely to distinguish one element, component, region, layer or section from another region, layer or section. Unless indicated in the context explicitly, terms such as "first", "second" and other similar terms and numerical terms, used herein do not imply a sequence or an order. Therefore, the first element, component, region, layer or section discussed thereafter may be referred to as a second element, component, region, layer or section without departing from the technical teachings of the exemplary embodiments.

For the convenience of description, spatially relative terms, such as "interior", "exterior", "inner side", "outer side", "under", "below", "over", "above", may be used herein to describe a relationship of one element or feature relative to another element or feature as shown in the drawings. Such spatially relative terms are intended to include different orientations of the device in use or operation in addition to the orientation depicted in the drawings. For example, if the device in the drawings is turned over, an element described as "under other elements or features" or "below other elements or features" will be then oriented "over other elements or features" or "above other elements or features". Thus, the exemplary term "below" may include both an upper and a lower orientation. The device may be oriented separately (rotated 90 degrees or in other directions) and may be interpreted accordingly according to the spatially relative descriptors used herein.

In the field of interventional medical instruments, one end of a medical device implanted into a human or animal body closer to an operator is generally referred to as a "proximal end" and one end farther from the operator is referred to as a "distal end"; and the "proximal end" and the "distal end" of any component of a medical device are defined according to this principle. An "axial direction" in the present application shall be understood as a direction in which the thrombus removal device is pushed; a direction perpendicular to the "axial direction" shall be defined as a "radial direction", and a "lengthwise direction" shall be understood as a direction in which the thrombus removal device has the longest physical dimension.

Embodiment 1

As shown in FIGS. 4-8, a thrombus removal device 300 is provided, including an elongated delivery member 301 and a plurality of elongated delivery members 302 disposed on the elongated delivery member 301; the thrombus removal member 302 has a compressed configuration and an expanded configuration formed from the compressed configuration by means of self-expansion. Each thrombus removal member 302 is assembled on the elongated delivery member 301 to form a thrombus removal functional section of the thrombus removal member 300. At least one thrombus removal member 302 among the plurality of thrombus removal members 302 on the thrombus removal functional section is rotatably connected to the elongated delivery member 301.

The thrombus removal device 300 provided in the present example may be contained in a microcatheter 102 in a compressed configuration. During the process of thrombus removal, the thrombus removal device 300 is delivered into a blood vessel 201 through the microcatheter 102 and reaches a further distal end of the blood vessel 201 after passing through the thrombus 202, and then the microcatheter 102 is withdrawn so that the thrombus removal device 300 expands in the blood vessel 201, in which the rotatable thrombus removal member 302 needs to be released and expanded at the thrombus 202. Since the thrombus removal member 302 is free to rotate relative to the elongated delivery member 301, the thrombus removal member 302 can be rotationally transformed into a more stable state under the interaction with the thrombus 202 and the blood vessel 201 during contact with the thrombus 202 due to its expansion. Therefore, the thrombus 202 is allowed to enter the thrombus entrance of the thrombus removal member 302, thus achieving the capture of the thrombus 202. In summary, by means of causing the thrombus removal member 302 to have rotational degrees of freedom, the thrombus removal device 300 provided by the present example enables a thrombus 202 to enter the thrombus removal member 302 more easily by means of a thrombus entrance so that the thrombus removal member 302 may fully expand and fully contact the thrombus 202, thereby achieving more effective capture of the thrombus 202.

Further, as shown in FIGS. 9-12, the thrombus removal member 302 includes a connecting member 3021 located at a proximal end thereof and a grid frame extending towards a distal direction from the connecting member 3021; and each grid on the grid frame is a thrombus entrance.

Specifically, the grid frame of the thrombus removal member 302 includes two first stent bars 3022 connected to the connecting member 3021, the two first stent bars 3022 extend towards a distal direction in a mutually-separated manner from a starting part which is the connection part between the first stent bars and the connecting member; an end of each of the first stent bars 3022 splits into two second stent bars 3023 extending towards a distal direction in a mutually-separated manner; ends of the two adjacent second stent bars 3023 which are split by the different first stent bars 3022 converge at a point. In a grid frame formed by first stent bars 3022 and second stent bars 3023, each closed grid forms a thrombus entrance, for example, a closed grid formed by two first stent bars 3022 and two second stent bars 3023 is a thrombus entrance 303; a closed grid formed by two first stent bars 3022 and another two second stent bars 3023 is another thrombus entrance 304; and a closed grid formed by four second stent bars 3023 is a third thrombus entrance 305. The two first stent bars 3022 form an included angle A1 which is between 7-180°, and preferably between 30-120°; the two second stent bars 3023 converging at a point form an included angle A2 which is between 7-180°, and preferably between 30-120°; the two second stent bars 3023 split by the same first stent bar 3022 form an included angle A3 which is between 7-180°, and preferably between 30-120°. During the process of thrombus removal, the thrombus removal member 302 may be roughly divided into two states relative to the position of the thrombus 202: one is that a frame surface formed by a first stent bar 3022 and two second stent bars 3023 is in frontal contact with the thrombus 202; another one is that a thrombus entrance formed by two first stent bars 3022 and two second stent bars 3023 is in frontal contact with the thrombus 202. It is envisaged that the thrombus 202 will enter the defined reach of the thrombus removal device 300 more readily when the thrombus entrance is in frontal contact with the thrombus 202.

A thrombus removal device 300 including three thrombus removal members 302 is used as an example to explain the thrombus removal process. As shown in FIG. 13, the thrombus removal member 302 located in the middle position has rotational degrees of freedom relative to the elongated delivery member 301:

a. as shown in FIGS. 13 (a) and 13 (b), a microcatheter 102 containing a thrombus removal device 300 has passed through the thrombus 202 to reach a further distal end of the blood vessel 201;

b. the thrombus removal device 300 passes through the microcatheter 102 to reach the blood vessel 201 at a distal end of the thrombus 202; and at this time, the thrombus removal device 300 is integrally in a compressed configuration;

c. as shown in FIG. 13 (c), the microcatheter 102 is withdrawn so that the thrombus removal device 300 expands in the blood vessel 201; and at this time, there is no thrombus 202 in the release positions of the two thrombus removal members 302 located at the proximal and distal sides, so the thrombus removal device expands fully. After the thrombus 202 is extruded, the proximal portion of the thrombus 202 enters the proximal thrombus removal member 302 which is located in a middle position from a thrombus entrance 305 of a proximal thrombus removal member 302. A frame surface formed by a first stent bar 3022 and two second stent bars 3023 is in frontal contact with the thrombus 202; and the thrombus 202 cannot directly enter the grid frame. At this time, an elongated delivery member 301 is slightly pushed and pulled in an axial direction, and the frame surface of the thrombus removal member 302 in the middle position tends to transform into a stable state under a certain external force;

d. as shown in FIG. 13 (d), the thrombus removal member 302 in the middle position rotates about the elongated delivery member 301 under the interaction of the elongated delivery member 301, the thrombus 202 and the blood vessel 201 so that the thrombus entrance 303 (or 304) contacts the thrombus 202. At this time, due to its greater size, the thrombus 202 may still extrude the thrombus removal member 302 in the middle position; and then the elongated delivery member 301 is pushed and pulled back and forth continuously and gently;

e. the elongated delivery member 301 carries the thrombus removal member 302 in the middle position and the thrombus 202 to make slight relative movement while the thrombus removal member 302 continues to slowly self-expand, thus gradually framing the thrombus 202 within the grid frame of the thrombus removal member 302 (as shown in FIG. 13 (e));

f. finally, the thrombus removal device 300 is withdrawn to remove the thrombus 202.

It should be noted that the number of first stent bars 3022 emitted from the connecting member 3021 may also be 3, 4 or more, preferably 2 to 6.

Preferably, the length of the first stent bar 3022 may be made smaller than that of the second stent bar 3023, thus allowing the thrombus removal member 302 to rotate more easily under an external force.

Figure 14:
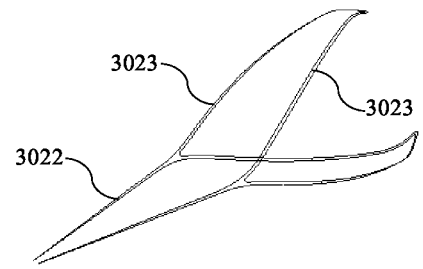
FIG. 14 is a schematic diagram showing a structure of the grid frame in Example 1.
Figure 15:
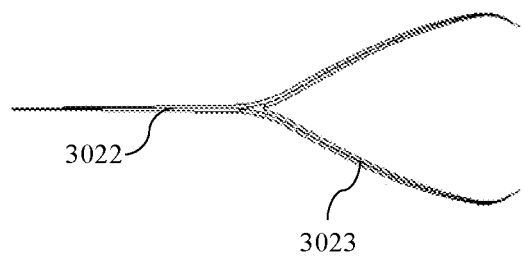
FIG. 15 is a schematic front view of FIG. 14.

Preferably, as shown in FIGS. 14 and 15, to decrease the damage of the thrombus removal device 300 to the blood vessel 201 during thrombus removal, each distal convergence point of the grid frame tends to converge towards a central axis of the grid frame.

Figure 16:
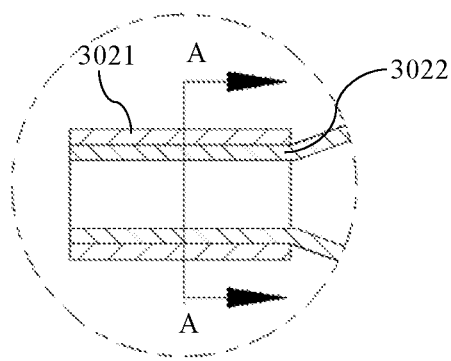
FIG. 16 is a schematic diagram showing a connection relationship between the connecting member and the first stent bar.
Figure 17:
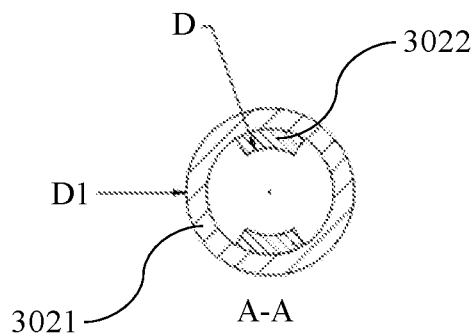
FIG. 17 is a schematic sectional view taken along line A-A of FIG. 16.

Further, the connection relation between the connecting member 3021 and the first stent bar 3022 may be in various forms, and will be described by the following examples hereafter:

In one embodiment, as shown in FIGS. 16 and 17, a cross section of the connecting member 3021 is substantially annular; and the first stent bar 3022 is connected to the cross section in the interior of the connecting member 3021 by welding, riveting, bonding, and the like. A connecting portion formed with the connecting member 3021 and the elongated delivery member 301 has a minimum inner diameter D and a maximum outer diameter D1, and D and D1 are respectively 0.05-0.5 mm and 0.05-0.5 mm. It is envisaged that D1 is greater than D within the same thrombus removal member 302; and D is greater than the outer diameter of the connecting portion of the elongated delivery member 301.

Figure 18:
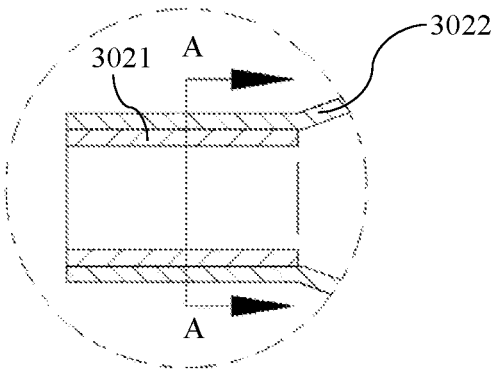
FIG. 18 is a schematic diagram showing another connection relationship between the connecting member and the first stent bar.
Figure 19:
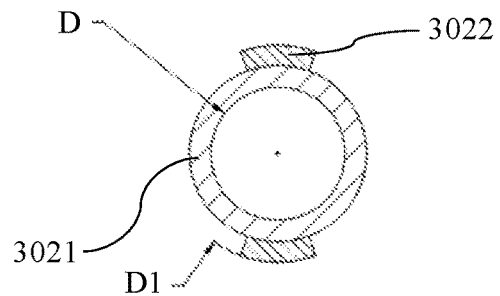
FIG. 19 is a schematic sectional view taken along line A-A of FIG. 18.

In another embodiment, as shown in FIGS. 18 and 19, a cross section of the connecting member 3021 is substantially annular; and the first stent bar 3022 is connected to the cross section in the exterior of the connecting member 3021 by welding, riveting, bonding, and the like. A connecting portion formed with the connecting member 3021 and the elongated delivery member 301 has a minimum inner diameter D and a maximum outer diameter D1; and D and D1 are respectively 0.05-0.5 mm and 0.05-0.5 mm. It is envisaged that D1 is greater than D within the same thrombus removal member 302; and D is greater than the outer diameter of the connecting portion of the elongated delivery member 301.

Figure 20:
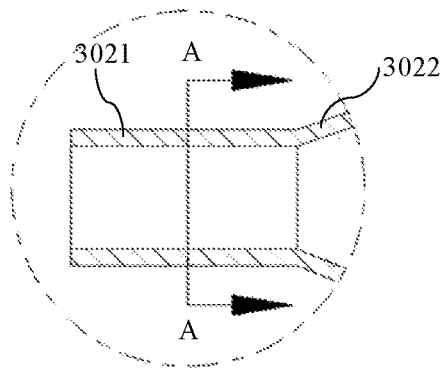
FIG. 20 is a schematic diagram showing another connection relationship between the connecting member and the first stent bar.
Figure 21:
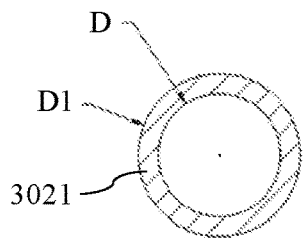
FIG. 21 is a schematic sectional view taken along line A-A of FIG. 20.

In another embodiment, as shown in FIGS. 20 and 21, a cross section of the connecting member 3021 is substantially annular, and the first stent bar 3022 is connected to the cross section on an end portion of connecting member 3021 by welding, riveting, bonding, and the like (alternatively, the first stent bar 3022 and the connecting member 3021 may be engraved in the same tube by laser engraving). A connecting portion formed with the connecting member 3021 and the elongated delivery member 301 has a minimum inner diameter D and a maximum outer diameter D1; and D and D1 are respectively 0.05-0.5 mm and 0.05-0.5 mm. It is envisaged that D1 is greater than D within the same thrombus removal member 302; and D is greater than the outer diameter of the connecting portion of the elongated delivery member 301.

Figure 22:
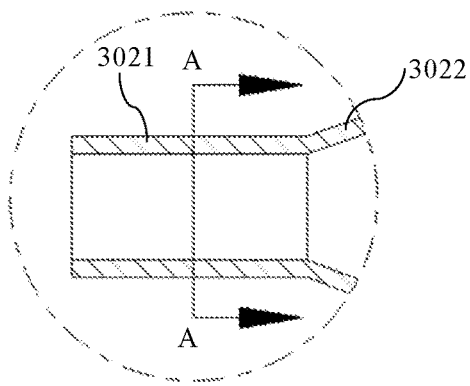
FIG. 22 is a schematic diagram showing another connection relationship between the connecting member and the first stent bar.
Figure 23:
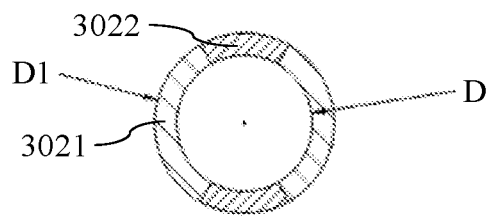
FIG. 23 is a schematic sectional view taken along line A-A of FIG. 20.
Figure 24:
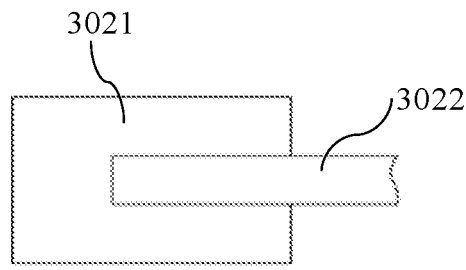
FIG. 24 is a top schematic view of FIG. 22.

In another embodiment, as shown in FIGS. 22-24, a cross section of the connecting member 3021 is substantially annular. First, a groove (a through groove or a non-through groove in the thickness direction is available) is engraved on a surface of the connecting member 3021. Then, the first stent bar 3022 is placed into the groove of the connecting member 3021 and connected by welding, riveting, bonding, and the like. A connecting portion formed with the connecting member 3021 and the elongated delivery member 301 has a minimum inner diameter D and a maximum outer diameter D1; and D and D1 are respectively 0.05-0.5 mm and 0.05-0.5 mm. It is contemplated that D1 is greater than D within the same thrombus removal member 302; and D is greater than the outer diameter of the connecting portion of the elongated delivery member 301.

Figure 25:
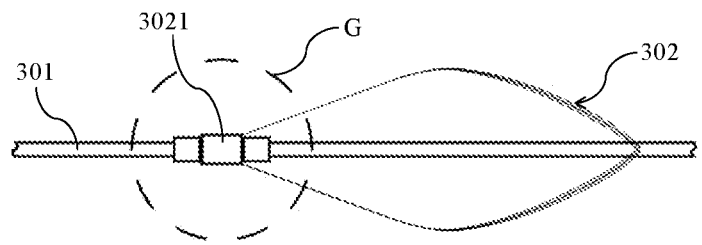
FIG. 25 is a schematic diagram showing a structure of the thrombus removal member having rotational degrees of freedom.
Figure 26:
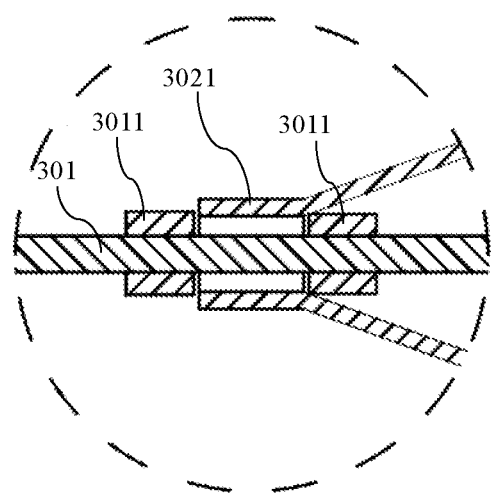
FIG. 26 is a schematic diagram showing an enlarged view of a portion G in FIG. 25.
Figure 27:
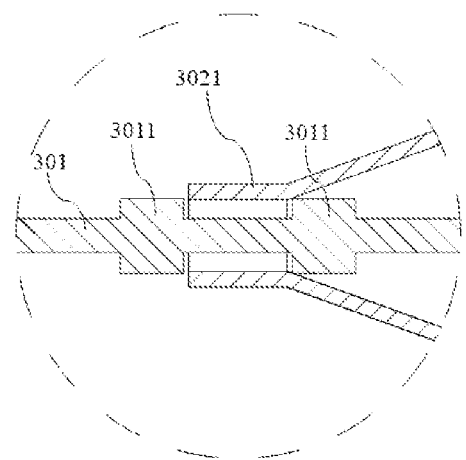
FIG. 27 is a schematic diagram showing another enlarged structure of the portion G in FIG. 25.
Figure 28:
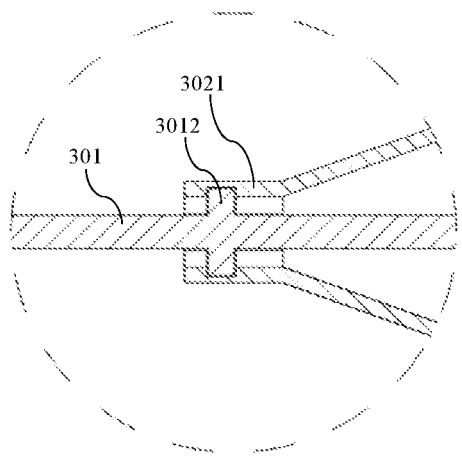
FIG. 28 is a schematic diagram showing another enlarged structure of the portion G in FIG. 25.

Further, to achieve the rotatable connection of at least one thrombus removal member 302 with the elongated delivery member 301, as shown in FIGS. 24 and 25, a feasible embodiment is as follows: a connecting member 3021 of at least one thrombus removal member 302 is a sleeve, and the elongated delivery member 301 passes through the sleeve, and a space is reserved between the elongated delivery member 301 and the sleeve. Two limiting pieces 3011 are further arranged on the elongated delivery member 301, and the two limiting pieces 3011 are respectively located at proximal sides and distal sides of the sleeve, thus limiting the moving degrees of freedom of the sleeve on the elongated delivery member 301 in an axial direction. Specifically, the limiting piece 3011 may be an annular member separated from the elongated delivery member 301 as shown in FIG. 26; and the limiting piece can be positioned to surround the elongated delivery member 301 and fixedly connected thereto by welding, riveting, bonding, and the like; or as shown in FIG. 27, the limiting piece 3011 is a bulge on the elongated delivery member with the same material. The cross section of the bulge perpendicular to the axis of the elongated delivery member 301 may be circular, semi-circular, ⅓ circular, square, and the like. The cross section should satisfy the following conditions: if a circle is drawn with the midpoint of the elongated delivery member 301 as a center of the circle, and with the distance of the cross section farthest from the center of the circle as a radius, the diameter of the circle should be greater than the minimum inner diameter of the connecting member 3021 of the thrombus removal member 302 at the same location. FIG. 28 shows another way of assembling the limiting piece 3011 with the connecting member 3021 of the thrombus removal member 302: the connecting member 3021 has a groove extending towards an outer side of the connecting member 3021 from an inner side thereof; and the limiting piece 3012 disposed on the elongated delivery member 301 is clamped into the groove so that the thrombus removal member 302 cannot move along the axis of the elongated delivery member 301.

Figure 29:
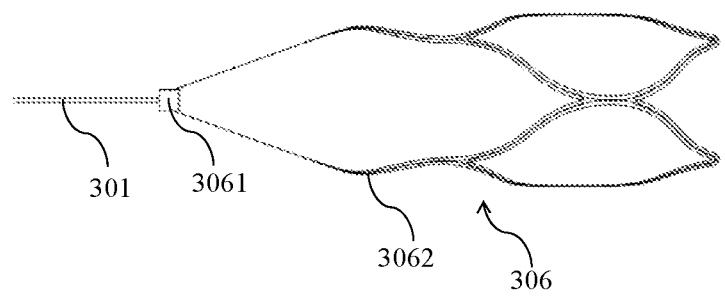
FIG. 29 is a schematic diagram showing a structure of an anti-falling member.

Further, the thrombus removal device 300 further includes an anti-falling member 306 configured at a distal end of the elongated delivery member 301 (as shown in FIG. 29); the anti-falling member 306 includes a second connecting member 3061 located at a proximal end and a second grid frame 3062 extending towards a distal direction from the second connecting member 3061; and the second grid frame 3062 has at least two sets of grids in an axial direction. Further, the anti-falling member 306 and each of the thrombus removal members 302 constitute a main body of the thrombus removal device 300; the main body has a length L3 of between 15-60 mm, and preferably between 15-40 mm, 35-40 mm, and 25-60 mm (corresponding to three different specifications of thrombus removal devices 300) and the like. The thrombus removal device 300 has a maximum radial diameter of between 2-6 mm, and preferably between 2-3 mm, 3-4 mm, 5-6 mm, and the like. A single thrombus removal member 302 has a length L1 of between 3-20 mm without an external force.

Preferably, the density of the distal grids on the second grid frame 3062 is greater than the density of the proximal grids.

Figure 30:
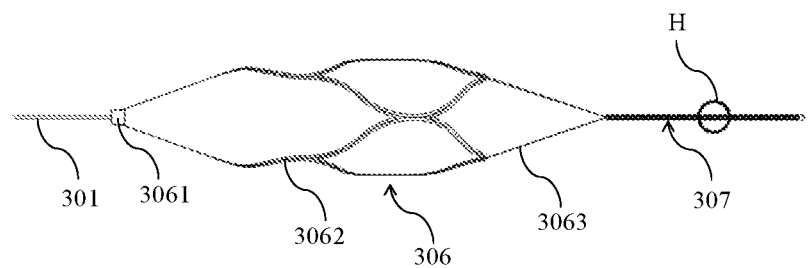
FIG. 30 is a schematic diagram showing a structure of the thrombus removal device provided with a guide section.
Figure 31:
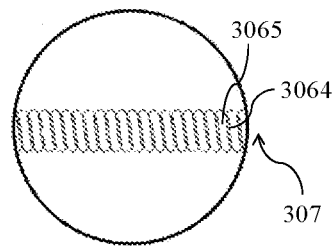
FIG. 31 is a schematic diagram showing an enlarged portion H in FIG. 30.
Figure 32:
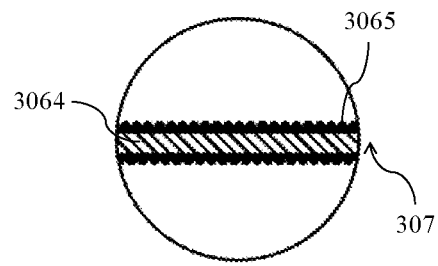
FIG. 32 is a cross-sectional view showing the structure as shown in FIG. 31.

In another example, as shown in FIGS. 30-32, a plurality of stent bars 3063 are arranged on a distal end of the anti-falling member 306; and distal ends of the plurality of stent bars 3063 converge together to form a stent bar bundle 3064, so that both proximal and distal ends of the anti-falling member 306 form a closed frame structure. Preferably, a spring 3065 is wound around the exterior of the stent bar bundle 3064, and the stent bar bundle 3064 and the spring 3065 constitute a guide section 307 of the thrombus removal device 300; the guide section 307 has better flexibility compared with other portions of the thrombus removal device 300, and is configured on the most distal end of the thrombus removal device 300 to facilitate the reduction of damage to the blood vessel 201 by the thrombus removal device 300. More preferably, the stent bar 3063 is made of a material having good elasticity, such as nickel-titanium alloy, stainless steel, cobalt-chromium alloy or other metal or high polymer materials having good elasticity; and may have a diameter of between 0.005 to 0.2 mm. The spring 3065 is made of a metal material having a relatively high molecular weight, such as gold, silver, copper, tungsten, and the like; the material has an outer diameter in a range from 0.005 to 0.5 mm; and the guide section 307 has an outer diameter in a range from 0.01 to 0.2 mm.

Figure 33:
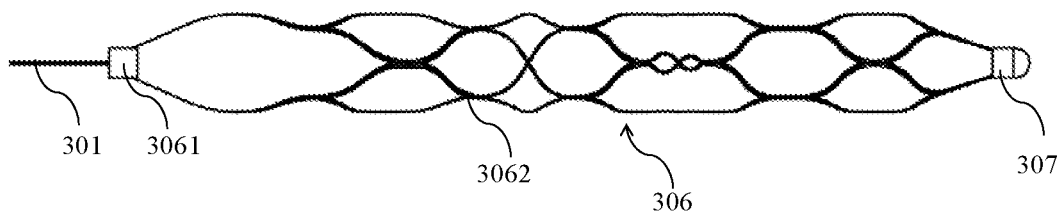
FIG. 33 is a schematic view showing another structure of the anti-falling member.

In another example, as shown in FIG. 33, a second grid frame 3062 of the anti-falling member 306 has two sets of grids above in an axial direction, and a guide section 307 is arranged on a distal end of the anti-falling member 306; and the guide section 307 is a structure having a closed end portion.

Further, the elongated delivery member 301 is a push-pull wire which may be made of a metal having good elasticity, including stainless steel, nickel-titanium alloy, cobalt-chromium alloy, and the like; and the push-pull wire has a diameter of not greater than 0.5 mm, preferably in a range from 0.05 to 0.4 mm.

Further, a developing device 308 is arranged on the thrombus removal member 302; the developing device 308 may annularly surround the second stent bar 3023 or may be filamentously wound around the second stent bar 3023.

Further, the radial force can be adjusted by adjusting the width of the first stent bar 3022 at the proximal end and the second stent bar 3023 at the distal end; the width of the first stent bar 3022 is in a range from 0.04 to 0.2 mm, preferably from 0.04 to 0.08 mm, 0.05 to 0.10 mm, 0.06 to 0.12 mm, and the like; and the width of the second stent bar 3023 is in a range from 0.03 to 0.15 mm, preferably from 0.03 to 0.06 mm, 0.04 to 0.08 mm, 0.06 to 0.12 mm, and the like.

Further, the thrombus removal member 302 and the anti-falling member 306 of the thrombus removal device 300 are formed by laser cutting a metal tube having a shape memory effect and superelasticity (e.g. a NiTi alloy tube), molding by a die, and shaping by heat treatment. Certainly, the processing may also be performed by cutting a metal sheet having a shape memory effect and superelasticity, molding by a die, and shaping by heat treatment. Further, the processing may also be performed by weaving and/or welding, cementing a metal wire having a shape memory effect and superelasticity, molding by a die, and shaping by heat treatment. The thrombus removal member 302 and the anti-falling member 306 may also be made of a high-elasticity polymer material. The above proper materials are well known to those skilled in the art and will not be described in detail herein.

Further, to reduce the damage of the thrombus removal device 300 to the vascular wall during thrombus removal, the outer surface of the thrombus removal device 300 may be coated with an inorganic biocompatible film "TiN" or an organic hydrophilic film "PTFE" or other hydrophilic polymer films. If a film is coated to the thrombus removal device 300, the thrombus removal device 300 must be polished, thus improving the surface smoothness of the thrombus removal device 300, reducing the coefficient of contact friction between the thrombus removal device 300 and the inner wall of the blood vessel, decreasing the withdrawal resistance of the thrombus removal device 300, and reducing the damage to the blood vessel wall; preferably, electrochemical polishing is selected.

Embodiment 2

Figure 34:
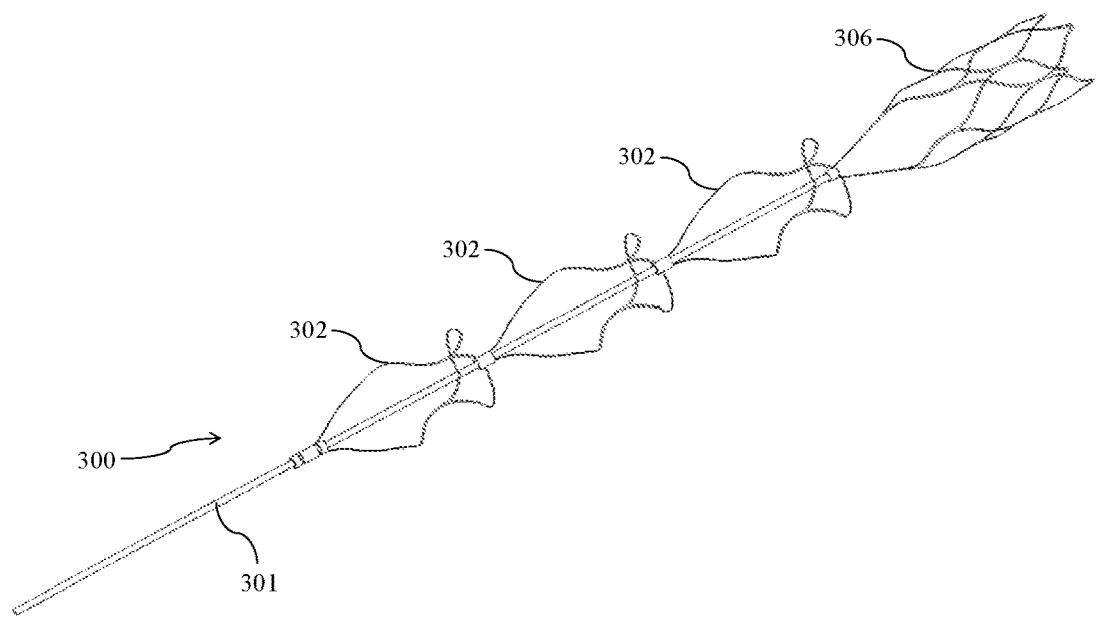
FIG. 34 is a schematic diagram showing a thrombus removal device in Example 2.
Figure 35:
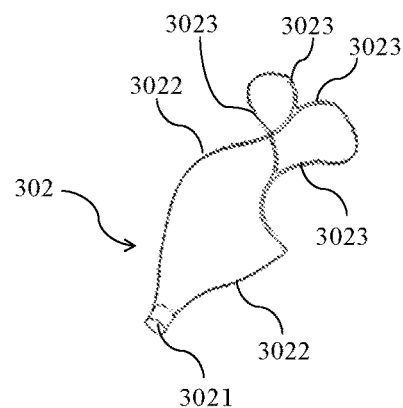
FIG. 35 is a schematic diagram showing a thrombus removal member in Example 2.

The same portion of the thrombus removal device 300 in Example 2 as that in Example 1 will not be described in detail herein; and Example 2 mainly differs from Example 1 in that: as shown in FIGS. 34 and 35, in Example 2, the grid frame includes a plurality (e.g. two, three, four or more) of first stent bars 3022 connected to the connecting member 3021; the plurality of first stent bars 3022 extend towards a distal direction in a spirally mutually-separated manner starting from connecting portions with the connecting member 3021; and the spiral direction of each of the first stent bars is the same; an end of each of the first stent bars splits into two second stent bars 3023 extending towards a distal direction in a mutually-separated manner; and ends of the two adjacent second stent bars 3023 which are split by the different first stent bars 3022 converge at a point.

In the thrombus removal device 300 of Example 2, since the first stent bars 3022 extend towards a distal direction in a spirally mutually-separated manner, and the spiral directions of the first stent bars 3022 are the same, therefore, the thrombus removal member 302 rotates more easily under an external force.

Figure 36:
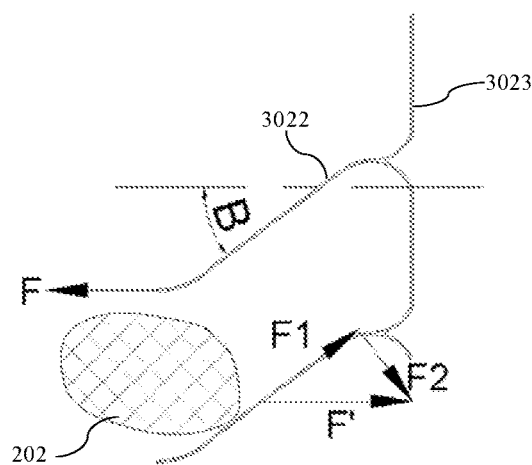
FIG. 36 is a diagram showing that the thrombus removal member as shown in FIG. 35 expands around its central axis.

FIG. 36 is a diagram showing that the thrombus removal member 302 expands around its central axis; in the figure, the thrombus removal member 302 has two first stent bars 3022 that form an angle B with the central axis. The thrombus removal member 302 contacts the thrombus 202 during thrombus removal; at this time, the elongated delivery member 301 exerts an acting force F to the thrombus removal member 302; and the thrombus 202 exerts a hindering effect on the first stent bar 3022 of the thrombus removal member 302 to generate an acting force F' opposite to F on the first stent bar 3022. Since the first stent bar 3022 and the central axis of the thrombus removal member 302 form an angle B, the acting force F' generates two component forces F1 and F2; and under the action of component force F2, the thrombus removal member 302 makes a rotational motion around the central axis, so that the thrombus 202 falls into the thrombus entrance of the thrombus removal member 302. Further, the angle B may be in the range of 1-89°. However, if the value of B is too small, the rotation angle becomes smaller, which is not conducive to the capture of the thrombus 202. The greater the value of B is, the smaller the corresponding force component F2 is, which makes it more difficult for the thrombus removal member 302 to rotate. Thus, the value of B has a preferred range of 25-65°.

Figure 37:
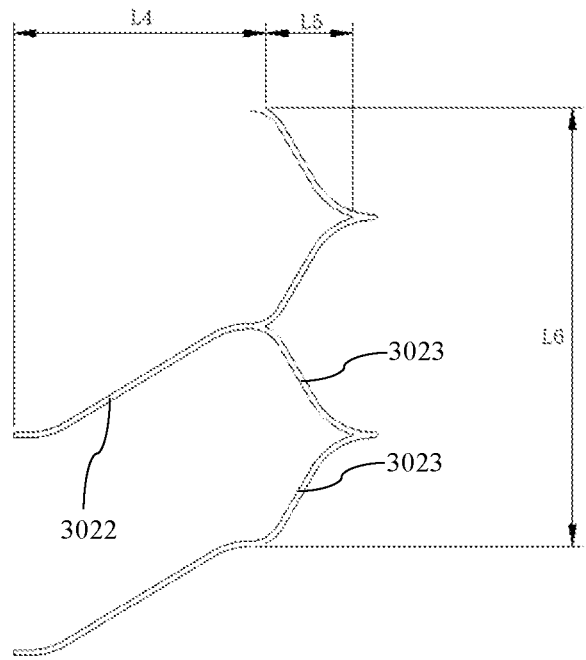
FIG. 37 is a schematic diagram showing that a distal converging portion of second stent bars is a "V"-shaped structure.

Further, the thrombus removal device 300 is delivered to a lesion site through the microcatheter 102 so that each thrombus removal member 302 of the thrombus removal device 300 has better deformability. As shown in FIG. 37, distal converging portions of the second stent bars 3023 form a "V"-shaped structure; an opening of the "V"-shaped structure is towards the proximal end of the thrombus removal member 302; and an included angle formed by the inner tangents on both sides of the "V"-shaped structure increases first and then decreases from the proximal direction to the distal direction of the thrombus removal member 302.

The structure of the thrombus removal member 302 shown in FIG. 37 may be divided into a frame selecting section and a blocking section based on the functional characteristics thereof. The frame selecting section has a length L4, the blocking section has a length L5, and both are subject to 3 mm≤L4+L5≤20 mm. The thrombus removal member 302 has a length L6 when expanded in a plane state around its central axis. If L4 is too short and L5 is too long, a slight deformation of the proximal end of the thrombus removal member 302 may result in greater deformation of the distal end thereof, and meanwhile, the overall radial force of the thrombus removal member 302 may be slightly lower. If L4 is too long and L5 is too short, the thrombus removal member 302 has a larger radial force, which can easily damage a blood vessel; therefore, L5 should be subject to 0.02 L6≤L5≤1.5 L6.

Embodiment 3

Figure 38:
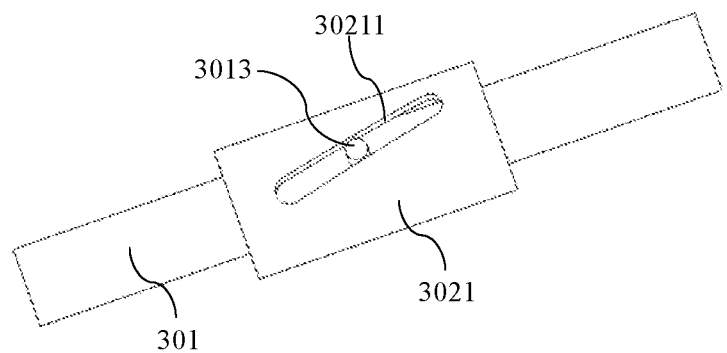
FIG. 38 is a 3D schematic diagram showing a connection relationship between a connecting member and an elongated delivery member in Example 3.

The same portion of the thrombus removal device 300 in Example 3 as that in Example 1 or 2 will not be described in detail herein; and Example 3 mainly differs from Example 1 or 2 in that: as shown in FIG. 38, in Example 3, the thrombus removal member 302 rotatably connected to the elongated delivery member 301 further has moving degrees of freedom along with the axial direction of the elongated delivery member 301. The connecting member 3021 is a sleeve which surrounds the elongated delivery member 301 in a clearance fit mode. A guide groove 30211 spirally extending towards the distal end from the proximal end is arranged on an inner wall of the sleeve, and a limiting piece 3013 in sliding fit with the guide groove 30211 is arranged on the elongated delivery member 301.

In Example 3, when the elongated delivery member 301 is pushed and pulled during thrombus removal, the thrombus removal member 302 having both rotational and moving degrees of freedom rotates more easily under the action of the elongated delivery member 301.

Figure 39:
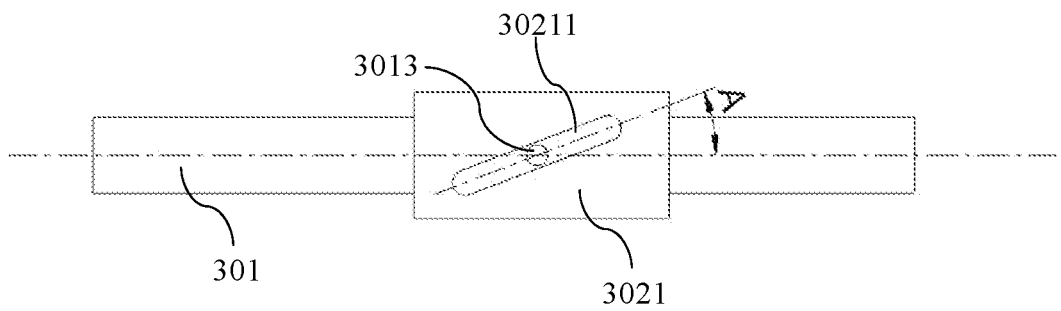
FIG. 39 is a schematic front view of FIG. 38.
Figure 40:
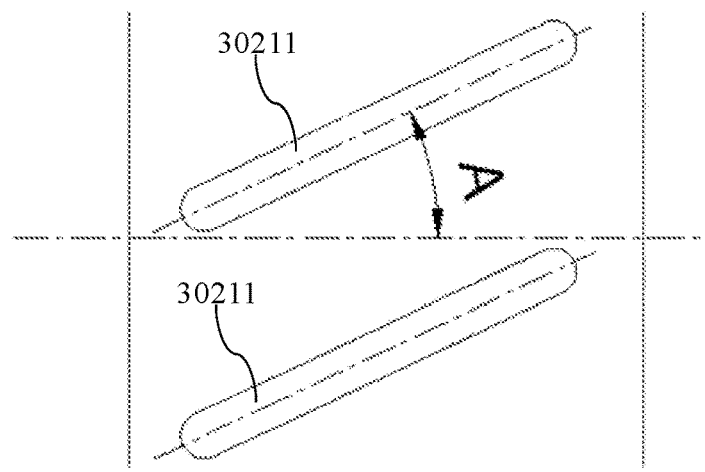
FIG. 40 is an expanded view of a connecting member (sleeve) as shown in FIG. 38.

Specifically, as shown in FIG. 39, the sleeve has at least one slanted guide groove 30211 forming an angle A with the axis; the guide groove 30211 extends towards the outer surface from the inner surface of the sleeve (the sleeve may not be penetrated). When the elongated delivery member 301 is pushed back and forth, and withdrawn, the sleeve rotates under the tangential force of the limiting piece 3013, thereby driving the thrombus removal member 302 to rotate. FIG. 40 is an expanded view of a sleeve. To make the sleeve easier to rotate, A has a value in the range of 1-85°; and preferably 30-60°. The guide groove 30211 may be obtained by conventional machining methods, such as laser engraving, wire cutting, powder metallurgy, milling, electrical discharge machining.

It will be appreciated that the sleeve is provided with at least one guide groove 30211 to achieve the easy rotation of the thrombus removal device 300; further, to enhance the strength of the sleeve and to maintain good rotating features, the number of the guide grooves 30211 and corresponding limiting pieces 3013 is preferably 2-6.

Embodiment 4

Figure 41:
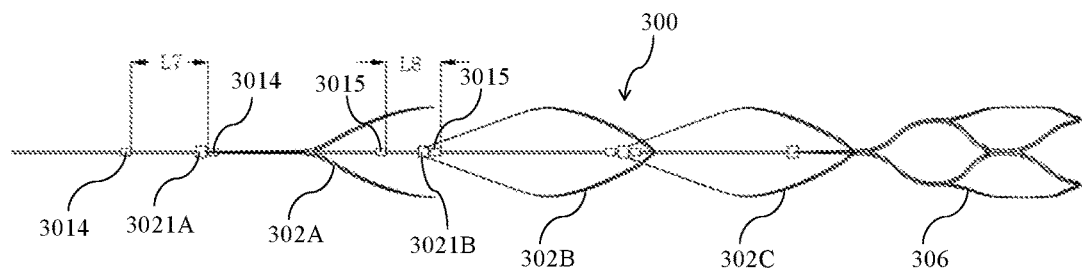
FIG. 41 is a schematic diagram showing a thrombus removal device in Example 4.

The same portion of the thrombus removal device 300 in Example 4 as that in Example 1 or 2 will not be described in detail herein; and Example 4 mainly differs from Example 1 or 2 in that: as shown in FIG. 41, in Example 4, the number of thrombus removal members 302 is three, and includes a first thrombus removal member 302A, a second thrombus removal member 302B and a third thrombus removal member 302C successively from the proximal end to the distal end; where, the first thrombus removal member 302A and second thrombus removal member 302B are rotatably connected to the elongated delivery member 301; further, the first thrombus removal member 302A and second thrombus removal member 302B can move towards a distal end from a proximal end or move towards a proximal end from a distal end along with the axial direction of the elongated delivery member 301; moreover, a movable range of the first thrombus removal member 302A is greater than that of the second thrombus removal member 302B. If the movable range of the first thrombus removal member 302A is L7 and the movable range of the second thrombus removal member 302B is L8, then L7 is greater than L8. It should be noted that the number of thrombus removal members 302 may also be adjusted according to specific requirements; for example, the number of thrombus removal members 302 may be two, four or other.

In Example 4, when the thrombus removal device 300 is pushed distally in the microcatheter 102, the first thrombus removal member 302A, the second thrombus removal member 302B and the third thrombus removal member 302C are tight and close to an inner wall of the microcatheter 102 due to their own self-expansion characteristic, so that the first thrombus removal member 302A and the second thrombus removal member 302B are located near the proximal end within respective movable ranges under the friction of the inner wall of the microcatheter 102. At this time, there is a maximum space between the first thrombus removal member 302A and the second thrombus removal member 302B, and between the second thrombus removal member 302B and the third thrombus removal member 3020. When the thrombus removal device 300 is fully released from the microcatheter 102, the thrombus 202 enters the grid frame of each thrombus removal member 302 of the thrombus removal device 300, and the thrombus removal device 300 is withdrawn proximally from the blood vessel 201; the first thrombus removal member 302A and the second thrombus removal member 302B move towards a distal direction within respective movable ranges under the friction of the inner wall of the blood vessel 201; when the first thrombus removal member 302A and the second thrombus removal member 302B move to the most distal position within respective movable ranges, there is a minimum space between the first thrombus removal member 302A and the second thrombus removal member 302B, and between the second thrombus removal member 302B and the third thrombus removal member 302C. Therefore, the space between the first thrombus removal member 302A and the second thrombus removal member 302B, and between the second thrombus removal member 302B and the third thrombus removal member 302C tends to decrease when the thrombus removal device 300 is withdrawn proximally from the blood vessel 201, thereby allowing the thrombus removal device 300 to clamp the thrombus 202 during withdrawal, and preventing the thrombus 202 from falling off the thrombus removal functional section.

Further, the connecting member on the first thrombus removal member 302A is a first sleeve 3021A; the connecting member on the second thrombus removal member 302B is a second sleeve 3021B; and both the first sleeve 3021A and the second sleeve 3021B are positioned about and surround the elongated delivery member 301 in a clearance fit mode; a first limiting piece 3014 is respectively arranged on the elongated delivery member 301 located at a proximal side and a distal side of the first sleeve 3021A; and a space is reserved between the two first limiting pieces 3014, so that the first thrombus removal member 302A can move towards the distal end from the proximal end or towards the proximal end from the distal end; a second limiting piece 3015 is respectively arranged on the elongated delivery member 301 located at a proximal side and a distal side of the second sleeve 3021B; a space is reserved between the two second limiting pieces 3015, so that the second thrombus removal member 302B can move towards the distal end from the proximal end or towards the proximal end from the distal end; and a space between the two first limiting pieces 3014 is greater than that between the two second limiting pieces 3015, so that the movable range of the first thrombus removal member 302A is greater than that of the second thrombus removal member 302B.

Embodiment 5

Figure 42:
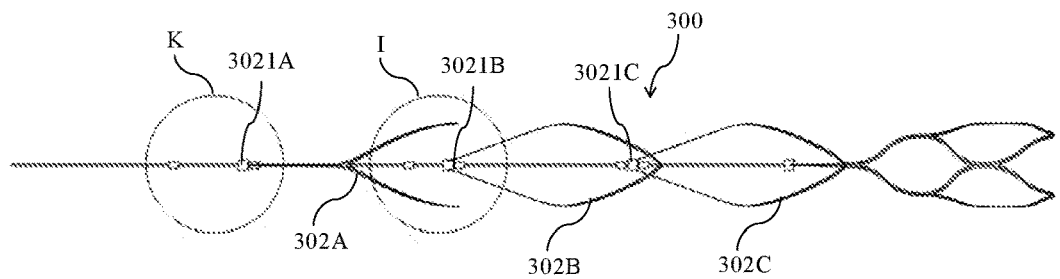
FIG. 42 is a schematic diagram showing a thrombus removal device in Example 5.
Figure 43:
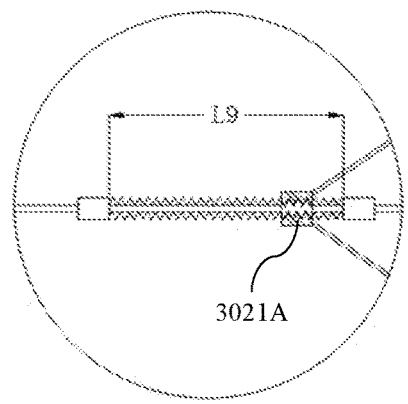
FIG. 43 is a schematic diagram showing an enlarged portion K in FIG. 42.
Figure 44:
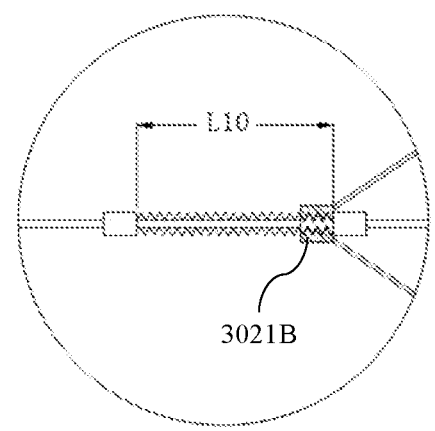
FIG. 44 is a schematic diagram showing an enlarged structure of a portion I in FIG. 42.

The same portion of the thrombus removal device 300 in Example 5 as that in Example 1 or 2 will not be described in detail herein; and Example 5 mainly differs from Example 1 or 2 in that: as shown in FIGS. 42-44, the number of the thrombus removal member 302 is three, and includes a first thrombus removal member 302A, a second thrombus removal member 302B and a third thrombus removal member 302C successively from the proximal end and the distal end; a connecting member on the first thrombus removal member 302A is a first sleeve 3021A, a connecting member on the second thrombus removal member 302B is a second sleeve 3021B, and a connecting member of the third thrombus removal member 302C is a third sleeve 3021C; and the third sleeve 3021C is positioned on and surrounds the elongated delivery member 301 in a clearance fit mode so that the third thrombus removal member 302C is allowed to rotate relative to the elongated delivery member 301. An axial movable range of the first sleeve 3021A is greater range than that of the second sleeve 3021B on the elongated delivery member 301. A first internal thread is arranged on an inner wall of the first sleeve 3021A; a second internal thread is arranged on an inner wall of the second sleeve 3021B; a first external thread and a second external thread, respectively coupled to the first internal thread and the second internal thread, are arranged on the elongated delivery member 301.

In Example 5, a pitch of the first internal thread is greater than that of the second internal thread. Further, a distribution range L9 of the first internal thread on the elongated delivery member 301 is greater than a distribution range L10 of the second internal thread.

The thrombus removal device 300 in Example 5 differs from that in Example 4 in that: when the elongated delivery member 301 is rotated, the first thrombus removal member 302A and the second thrombus removal member 302B can make a relative rectilinear motion with the elongated delivery member 301 under the action of the threads; compared with Example 4, the first thrombus removal member 302A and the second thrombus removal member 302B can rotate actively under the action of threads; the pitch of the first internal thread is greater than that of the second internal thread; where the elongated delivery member 301 is rotated for the same cycles, the moving distance of the first thrombus removal member 302A is greater than that of the second thrombus removal member 302B, so that two adjacent thrombus removal members 302 can be approached actively, thus clamping the thrombus 202 and preventing the thrombus 202 from falling off the thrombus removal functional section of the thrombus removal device 300 during withdrawal.

Figure 45:
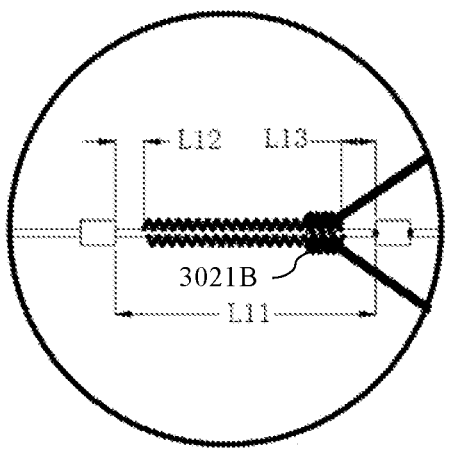
FIG. 45 is a schematic diagram showing another enlarged structure of the portion I in FIG. 42.

In another example, the pitch of the first internal thread may also be equal to the pitch of the second internal thread; an unthreaded portion (as shown in FIG. 45) should be arranged on both ends of the second sleeve 3021B within the axial movable range. This is because when the first internal thread and the second internal thread have the same pitch, and the elongated delivery member 301 rotates the same cycles, the first thrombus removal member 302A and the second thrombus removal member 302B move the same distance, when the second thrombus removal member 302B finishes the full travel distance, the first thrombus removal member 302A still has a partial travel distance that is not finished. If the elongated delivery member 301 is rotated continuously at this time, it is possible to cause the continued rotation of the second thrombus removal member 302B relative to the blood vessel 201, thereby increasing the risk of damaging the blood vessel 201. To avoid the above situation, two unthreaded portions (near both ends of the stroke range) may be disposed within the stroke range (L11) of axial movement of the second thrombus removal member 302B; with the unthreaded portions having lengths L12 and L13 respectively, and both L12 and L13 should be greater than the length of the second sleeve 3021B.

Embodiment 6

The same portion of the thrombus removal device 300 in Example 6 as that in Example 1 or 2 will not be described in detail herein; and Example 6 mainly differs from Example 1 or 2 in that: the thrombus removal device 300 includes a thrombus removal member 302 disposed on the elongated delivery member 301 and an anti-falling member 306 disposed on a distal end of the elongated delivery member 301, where the number of thrombus removal members 302 is one, and the thrombus removal member 302 is rotatably connected to the elongated delivery member 301.

In Example 6, the thrombus removal member 302 of the thrombus removal device 300 has rotational degrees of freedom relative to the elongated delivery member 301, thus achieving effective capture of the thrombus 202; and further, an anti-falling member 306 is combined to remove the thrombus 202.

The above Examples are only preferred embodiments of the present disclosure, rather than restricting the protection scope of the present disclosure. Any person skilled in the art can easily envisage variations or substitutions without departing from the spirit and scope of the present disclosure. Therefore, the protection scope of the present disclosure shall be determined by the scope as defined in the claims.

The invention claimed is:

1. A thrombus removal device, wherein the thrombus removal device comprises an elongated delivery member and a plurality of thrombus removal members disposed on the elongated delivery member, each thrombus removal member among the plurality of thrombus removal members having a compressed configuration and an expanded configuration formed from the compressed configuration by means of self-expansion; and at least one thrombus removal member among the plurality of thrombus removal members is rotatably connected to the elongated delivery member, wherein the plurality of thrombus removal members comprise at least a first thrombus removal member and the second thrombus removal member, wherein the first thrombus removal member and the second thrombus removal member are rotatably coupled to the elongate delivery member, and a thrombus can be clamped between the first thrombus removal member and the second thrombus removal member;

wherein the first thrombus removal member and the second thrombus removal member each comprises:
a connecting member located at a proximal end of the thrombus removal member; and
a grid frame extending towards a distal direction from the connecting member; the grid frame of the thrombus removal member comprises a plurality of first stent bars connected to the connecting member; the plurality of first stent bars extend towards a distal direction in a spirally mutually-separated manner from a starting part which is the connection part between each of the first stent bars and the connecting member; and
wherein each of the plurality of first stent bars comprises an end of the first stent bar that is split into two second stent bars extending in the distal direction in a mutually separated manner, and
among a plurality of second stent bars separated by two adjacent first stent bars, two adjacent second stent bar ends separated by different first stent bars meet at a point forming a V-shaped structure; and
an included angle formed by the inner tangents on both curved sides of the "V"-shaped structure increases first and then decreases from a proximal direction to the distal direction of the thrombus removal member.

2. The thrombus removal device of claim 1, wherein the first thrombus removal member and the second thrombus removal member are movable from a proximal end to a distal end or from a distal end to a proximal end along an axial direction of the elongate delivery member, the first thrombus removal member and the second thrombus removal member each having a movable range, the movable range of the first thrombus removal member being greater than the movable range of the second thrombus removal member.

3. The thrombus removal device of claim 1, wherein the connecting member on the first thrombus removal member is a first sleeve, the connecting member on the second thrombus removal member is a second sleeve, and the first sleeve and the second sleeve respectively surround the elongate delivery member in a clearance-fitting manner.

4. The thrombus removal device of claim 3, wherein on the elongate delivery member, a first limiting piece is provided on a proximal side and a distal side of the first sleeve, respectively, with a distance between the first limiting piece provided on the proximal side and the first limiting piece provided on the distal side of the first sleeve to enable movement of the first thrombus removal member from a proximal end to a distal end or from the distal end to the proximal end;
on the elongate delivery member, a second limiting piece is provided on a proximal side and a distal side of the second sleeve, respectively, with a distance between the second limiting piece provided on the proximal side and the second limiting piece provided on the distal side of the second sleeve to enable movement of the second thrombus removal member from the proximal end to the distal end or from the distal end to the proximal end.

5. The thrombus removal device of claim 4, wherein the first sleeve is provided with a first internal thread, the second sleeve is provided with a second internal thread, a first external thread and a second external thread respectively cooperating with the first internal thread and the second internal thread are provided on the elongate delivery member, the first external thread has a distribution range, the second external thread has a distribution range, the distribution range of the first external thread on the elongate delivery member is larger than the distribution range of the second external thread, a screw pitch of the first internal thread is equal to a screw pitch of the second internal thread, and parts without threads are provided at both the proximal side and the distal side of the first sleeve and both the proximal side and the distal side of the second sleeve within a range of axial movement of the second sleeve.

6. The thrombus removal device of claim 5, wherein the parts without threads have a length and the second sleeve has a length, and wherein the length of the parts without threads is greater than the length of the second sleeve.

7. The thrombus removal device of claim 1, wherein the first thrombus removal member and the second thrombus removal member are provided with a radiopaque device, and the radiopaque device surrounds the plurality of second stent bars or the radiopaque device is wound around the plurality of second stent bars second stent rod in a wire shape.

8. A thrombus removal device, wherein the thrombus removal device comprises an elongated delivery member and at least one thrombus removal member disposed on the elongated delivery member, each of the at least one thrombus removal member having a compressed configuration and an expanded configuration formed from the compressed configuration by means of self-expansion; and the at least one thrombus removal member is rotatably connected to the elongated delivery member;

wherein the at least one thrombus removal member comprises:
a connecting member located at a proximal end of the at least one thrombus removal member and
a grid frame extending towards a distal direction from the connecting member; the grid frame of the at least one thrombus removal member comprises a plurality of first stent bars connected to the connecting member; the plurality of first stent bars extend towards a distal direction in a spirally mutually-separated manner from a starting part which is the connection part between each of the first stent bars and the connecting member; and
wherein each of the plurality of first stent bars comprises an end of the first stent bar that is split into two second stent bars extending in the distal direction in a mutually separated manner, and
among a plurality of second stent bars separated by two adjacent first stent bars, two adjacent second stent bar ends separated by different first stent bars meet at a point forming a V-shaped structure; and
an included angle formed by the inner tangents on both curved sides of the "V"-shaped structure increases first and then decreases from a proximal direction to the distal direction of the at least one thrombus removal member.

9. The thrombus removal device of claim 8, wherein the wherein the at least one thrombus removal member is provided with a radiopaque device, and the radiopaque device is sleeved on the plurality of second stent bars or the radiopaque device is wound around the plurality of second stent bars in a wire shape.

10. The thrombus removal device of claim 8, wherein the at least one thrombus removal member sequentially comprises at least a first thrombus removal member and a second thrombus removal member from a proximal end and a distal end, wherein the first thrombus removal member and the second thrombus removal member are rotatably coupled to the elongate delivery member, and a thrombus can be clamped between the first thrombus removal member and the second thrombus removal member.

11. The thrombus removal device of claim 10, wherein the first thrombus removal member and the second thrombus removal member are movable from the proximal end to the distal end or from the distal end to the proximal end along an axial direction of the elongate delivery member, the first thrombus removal member and the second thrombus removal member each having a movable range, the movable range of the first thrombus removal member being greater than the movable range of the second thrombus removal member.

12. The thrombus removal device of claim 10, wherein the connecting member on the first thrombus removal member is a sleeve, the connecting member on the second thrombus removal member is a second sleeve, and the first sleeve and the second sleeve respectively surround the elongate delivery member in a clearance-fitting manner.

13. The thrombus removal device of claim 12, wherein the first sleeve is provided with a first internal thread, the second sleeve is provided with a second internal thread, and the elongated delivery member is provided with a first external thread and a second external thread respectively matched with the first internal thread and the second internal thread, wherein each of the first internal thread and the second internal thread respectively has a screw pitch, and the screw pitch of the first internal thread is equal to the screw pitch of the second internal thread.

14. The thrombus removal device of claim 12, wherein the first sleeve is provided with a first internal thread, the second sleeve is provided with a second internal thread, and the elongated delivery member is provided with a first external thread and a second external thread respectively matched with the first internal thread and the second internal thread, wherein each of the first internal thread and the second internal thread respectively has a screw pitch, wherein the screw pitch of the first internal thread is larger than the screw pitch of the second internal thread.

15. The thrombus removal device of claim 14, wherein the first external thread has a distribution range, the second external thread has a distribution range, and the distribution range of the first external thread on the elongated delivery member is greater than the distribution range of the second external thread.

16. The thrombus removal device of claim 12, wherein on the elongate delivery member, a first limiting piece is provided on a proximal side and a distal side of the first sleeve, respectively, with a first distance between the first limiting piece provided on the proximal side and the first limiting piece provided on the distal side of the first sleeve to enable movement of the first thrombus removal member from a proximal end to a distal end or from a distal end to a proximal end;
on the elongate delivery member, a second limiting piece is provided on a proximal side and a distal side of the second sleeve, respectively, with a second distance between the second limiting piece provided on the proximal side and the second limiting piece provided on the distal side of the second sleeve to enable movement of the second thrombus removal member from the proximal end to the distal end or from the distal end to the proximal end.

17. The thrombus removal device of claim 16, wherein the first sleeve is provided with a first internal thread, the second sleeve is provide with a second internal thread, a first external thread and a second external thread respectively cooperating with the first internal thread and the second internal thread are provided on the elongate delivery member, the first external thread has a distribution range, the second external thread has a distribution range, the distribution range of the first external thread on the elongate delivery member is larger than the distribution range of the second external thread, each of the first internal thread and the second internal thread respectively has a screw pitch ,wherein the screw pitch of the first internal thread is equal to the screw pitch of the second internal thread, and parts without threads are provided at both the proximal side and the distal side of the first sleeve and both the proximal side and the distal side of the second sleeve within a range of axial movement of the second sleeve.

18. A thrombus removal device of claim 17, wherein the parts without threads has a length, and the second sleeve has a length, wherein the length of the parts without threads is greater than the length of the second sleeve.

* * * * *